United States Patent
Kohiyama et al.

(10) Patent No.: US 10,883,985 B2
(45) Date of Patent: Jan. 5, 2021

(54) IMMUNOCHROMATOGRAPHIC TEST PIECE AND IMMUNOCHROMATOGRAPHY METHOD USING SAME

(71) Applicant: DENKA SEIKEN CO., LTD., Tokyo (JP)

(72) Inventors: Risa Kohiyama, Gosen (JP); Osamu Ishikawa, Gosen (JP); Yuki Shinohara, Gosen (JP); Takashi Miyazawa, Gosen (JP)

(73) Assignee: DENKA SEIKEN CO., LTD., Tokyo (JP)

( * ) Notice: Subject to any disclaimer, the term of this patent is extended or adjusted under 35 U.S.C. 154(b) by 272 days.

(21) Appl. No.: 15/575,455

(22) PCT Filed: May 20, 2016

(86) PCT No.: PCT/JP2016/064961
§ 371 (c)(1),
(2) Date: Dec. 22, 2017

(87) PCT Pub. No.: WO2016/186188
PCT Pub. Date: Nov. 24, 2016

(65) Prior Publication Data
US 2018/0172682 A1    Jun. 21, 2018

(30) Foreign Application Priority Data

May 21, 2015  (JP) ................................. 2015-103810

(51) Int. Cl.
*G01N 33/543*   (2006.01)
*G01N 33/558*   (2006.01)

(52) U.S. Cl.
CPC ..... *G01N 33/54393* (2013.01); *G01N 33/558* (2013.01)

(58) Field of Classification Search
CPC ................. G01N 33/54393; G01N 33/558
See application file for complete search history.

(56) References Cited

U.S. PATENT DOCUMENTS

| 4,672,045 A | 6/1987 | Tsutsui et al. |
| 6,426,182 B1 * | 7/2002 | Carrico .................. G01N 31/22 435/4 |
| 2010/0143933 A1 | 6/2010 | Minakawa et al. |

FOREIGN PATENT DOCUMENTS

| EP | 3032260 A1 | 6/2016 |
| JP | 63-67864 B2 | 12/1988 |
| JP | 2001-133456 A | 5/2001 |
| JP | 2002-31639 A | 5/2001 |
| JP | 2002-509254 A | 3/2002 |
| JP | 2005-241415 A | 3/2002 |
| JP | 2015-34719 A | 2/2015 |
| JP | 2015-210167 A | 11/2015 |
| WO | WO 99/36781 A1 | 7/1999 |

OTHER PUBLICATIONS

Machine translation of JP 2001-133456, published May 18, 2001.*
A printout retrieved from https://en.wikipedia.org/wiki/ Phosphate-buffered_saline on Jun. 10, 2020.*
International Search Report, issued in PCT/JP2016/064961, PCT/ISA/210, dated Aug. 16, 2016.
Written Opinion of the International Searching Authority, issued in PCT/JP2016/064961, PCT/ISA/237, dated Aug. 16, 2016.

* cited by examiner

*Primary Examiner* — Galina M. Yakovleva
(74) *Attorney, Agent, or Firm* — Birch, Stewart, Kolasch & Birch, LLP

(57) ABSTRACT

Disclosed is an immunochromatographic test strip by which the influences by the interfering substances in the immunochromatography method, contained in test samples, are reduced, so that it enables to accurately and specifically measure a test substance in a test sample irrespective of the amount of the test sample supplied to the assay, and to provide an immunochromatography method using the immunochromatographic test strip. The immunochromatographic test strip includes, in the order from upstream, a sample pad, a labeled substance region, a detection region and an absorption band, wherein a polymer(s) in which hydrophobic cyclic monomer(s) having an ionic functional group(s) is/are polymerized is impregnated at a region(s) upstream of the labeled substance region.

2 Claims, 1 Drawing Sheet

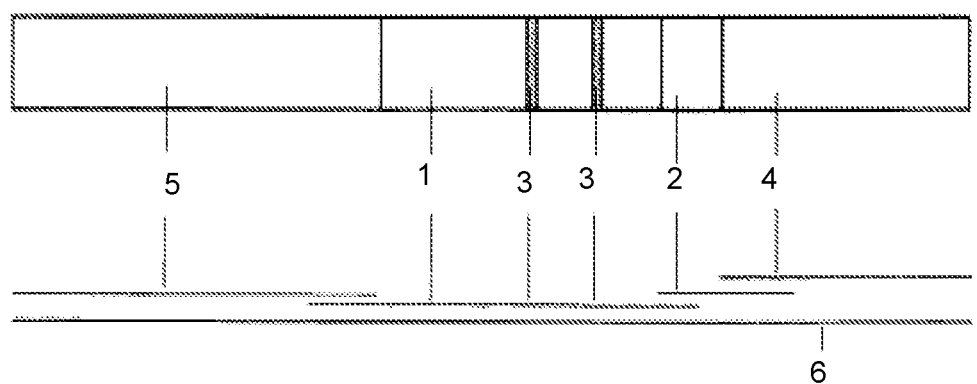

IMMUNOCHROMATOGRAPHIC TEST PIECE AND IMMUNOCHROMATOGRAPHY METHOD USING SAME

TECHNICAL FIELD

The present invention relates to an immunochromatographic test strip by which the influences by interfering substances contained in test samples are reduced, and to an immunochromatography method using the same.

BACKGROUND ART

Among clinical assays, there are many immunoassays whose test samples are biological samples, and it is known that interfering substances exist in the biological samples, which influence on the reactions with the ligands that bind to the test substances. To reduce the influence by the interfering substances, it has been reported to use an ionic surfactant having a molecular weight of 1000 to 100,000 (Patent Document 1).

The influence by the interfering substances may be seen as false negative or false positive in the quick diagnoses utilizing immunochromatography as the principle. Many of the quick diagnoses utilizing immunochromatography as the principle are widely used as means for quickly and simply detecting infectious diseases by viruses or bacteria, and for determining the policy of therapy. The above-mentioned false positive or false negative that occurs in the quick diagnoses utilizing immunochromatography as the principle may encourage a wrong therapy, slow the therapy, and may even lead to death.

Especially, false negatives prevent accurate diagnosis and therapy, so that they are very big problems. To prevent false positives and false negatives, a method has been reported in which the test sample is treated with a test sample-treating liquid containing a compound having two or more sulfate groups (Patent Document 2).

PRIOR ART REFERENCES

Patent Documents

Patent Document 1: JP 2005-241415 A
Patent Document 2: JP 2014-149189 A

SUMMARY OF THE INVENTION

Problems to be Solved by the Invention

An object of the present invention is to provide an immunochromatographic test strip by which the influences by the interfering substances in the immunochromatography method, contained in test samples, are reduced, so that it enables to accurately and specifically measure a test substance in a test sample irrespective of the amount of the test sample supplied to the assay, and to provide an immunochromatography method using the immunochromatographic test strip.

Means for Solving the Problems

The present inventors intensively studied to discover that a test substance in a test sample can be accurately and specifically measured reducing the influences by the interfering substances, by impregnating a polymer(s) in which hydrophobic cyclic monomer(s) having an ionic functional group(s) is/are polymerized in a specific site(s) in the immunochromatographic test strip, to complete the present invention.

That is, the present invention provides an immunochromatographic test strip comprising, in the order from upstream, a sample pad, a labeled substance region, a detection region and an absorption band, wherein a polymer(s) in which hydrophobic cyclic monomer(s) having an ionic functional group(s) is/are polymerized is impregnated at a region(s) upstream of the labeled substance region. The present invention also provides an immunochromatography method comprising using the immunochromatographic test strip according to the present invention.

Effects of the Invention

By the immunochromatographic test strip of the present invention, the influences by the interfering substances are reduced, so that it enables to accurately and specifically measure a test substance in a test sample irrespective of the amount of the test sample supplied to the assay.

BRIEF DESCRIPTION OF THE DRAWINGS

FIG. 1 is a view schematically showing the structure of a typical immunochromatographic test strip.

MODE FOR CARRYING OUT THE INVENTION

The present invention relates to an immunochromatographic test strip by which false positives and false negatives, especially false negatives are prevented, and accurate measurement of the test substance can be attained. Here, false positive means that a positive signal is generated in an assay in spite of the fact that a test substance is not contained in a test sample, and false negative means that a positive signal is not generated in an assay in spite of the fact that a test substance is contained in a test sample. For example, in immunochromatographic methods (immunochromatography methods), when the test substance is contained in the test sample, a complex of immobilized substance-test substance-labeling reagent is formed on a solid support, and the signal of the labeling substance from the complex is generated, while in the false negative, the generation of the signal is inhibited because of the reason that the complex is not formed or the like.

The immunochromatographic test strip comprises a support having a detection region in which an antibody (antibody 1) that captures a target to be measured (antigen or the like) is immobilized, a labeled substance region having a movable labeled antibody (antibody 2), a sample pad to which a sample is added dropwise, an absorption band which absorbs the developed sample liquid, and a backing sheet for attaching these members together.

The number of the detection regions and the type of the labeled antibodies included in the labeled substance region are not limited to 1. By using antibodies corresponding to a plurality of targets to be measured, two or more kinds of antigens can be measured by the same test strip.

FIG. 1 shows a preferred embodiment of a typical immunochromatographic test strip. It should be noted that the immunochromatographic test strip is not limited to that shown in FIG. 1. In FIG. 1, the reference numeral 1 denotes a support, the reference numeral 2 denotes a labeled substance region, the reference numeral 3 denotes a detection region, the reference numeral 4 denotes a sample pad, the reference numeral 5 denotes an absorption band and the reference numeral 6 denotes a backing sheet.

The upper figure in FIG. 1 is a top view and the lower figure is a cross-sectional view. In the example shown in the figures, the support in which two detection regions are formed, the absorption band, the labeled substance region and the sample pad are each laminated on the backing sheet. As shown in the figures, one end of the absorption band and one end of the support, the other end of the support and one end of the labeled substance region and the other end of the labeled substance region and one end of the sample pad are overlapped with each other so that a continuous lateral flow passage is formed.

The support is a material capable of immobilizing an antibody for capturing a test substance (antigen) and has a performance that does not prevent a liquid from passing in a horizontal direction. Preferably, the support is a porous thin film having a capillary action, and is a material capable of transporting a liquid and components dispersed therein by absorption. The material forming the support is not particularly limited, and examples thereof include cellulose, nitrocellulose, cellulose acetate, polyvinylidene difluoride (PVDF), glass fiber, nylon, polyketone and the like. Among them, a thin film made of nitrocellulose is more preferable.

The labeled substance region is made of a porous base material containing a labeled antibody, and a glass fiber, a nonwoven fabric or the like generally used can be used as the material of the base material. In order to impregnate a large amount of the labeled antibody, the base material is preferably in the form of a pad having a thickness of about 0.3 mm to 0.6 mm.

The detection region refers to a part of the support on which the antibody that captures the test substance (antigen) is immobilized. The detection region has at least one region in which the antibody for capturing the antigen is immobilized.

The sample pad is a site for dropping a specimen or a sample prepared using a specimen, and is a porous material having a water absorption property. Commonly-used cellulose, glass fiber, nonwoven fabric or the like can be used as the material. In order to use a large amount of the sample in the immunoassay, the material is preferably in the form of a pad having a thickness of about 0.3 mm to 1 mm. The sample pad and the above-mentioned labeled substance region are merely functional distinctions and need not necessarily be made of separate materials. That is, it is also possible that a partial area of the material set as the sample pad has the function of the labeled substance region.

The absorption band is a member for absorbing components that are supplied to the support and not involved in the reaction in the detection regions. As the material, a filter paper, a sponge or the like having high water retentivity made of a general natural polymer compound, synthetic polymer or the like can be used, but in order to promote development of the sample, one having high water absorbability is preferable.

The backing sheet is a member for attaching and fixing all the above-mentioned materials, i.e., the support, the sample pad, the labeled substance region, and the absorption band with a partial overlap. The backing sheet is not always necessary as long as these materials can be arranged and fixed at optimal intervals, but it is generally preferable to use the backing sheet in view of convenience in manufacturing and use.

In the test strip in the embodiment described with reference to FIG. 1, the sample passes through a porous flow passage formed by a series of connections of the sample pad, the labeled substance region, the support, the detection regions, and the absorption band. Therefore, in the present embodiment, all of them are sample moving regions. Depending on the quality and form of each constituent material, there may be a mode in which the sample does not penetrate the interior of the material but passes through the interface. However, since it does not matter whether the sample movement region defined in this specification is in the interior or the interface of the material, a test strip in such a mode is also included within the scope of this specification.

In the immunochromatographic test strip of the present invention, a polymer(s) in which hydrophobic cyclic monomer(s) having an ionic functional group(s) is/are polymerized is impregnated at a region(s) upstream of the labeled substance region (upstream along the flow of the test sample), that is, within the sample pad or between the sample pad and the labeled substance region. By this, the test substance in the test sample can be accurately and specifically measured irrespective of the amount of the test sample supplied to the assay.

The polymer(s) may be impregnated in the sample pad, or in a porous material other than the sample pad and the porous material may be arranged between the sample pad and the labeled substance region.

The polymer in which hydrophobic cyclic monomer(s) having an ionic functional group(s) is/are polymerized has the following characteristics.

The ionic functional group(s) may be an anionic functional group(s) or a cationic functional group(s). Preferred examples of the ionic functional group include sulfonic group and salts thereof, carboxyl group and salts thereof, and amines (quaternary amine or the like which is ionized in aqueous solution). Sulfonic group and salts thereof are especially preferred.

Examples of the hydrophobic ring include aromatic rings and cycloalkyl rings. The hydrophobic ring may be a hetero ring containing an oxygen atom(s), nitrogen atom(s), sulfur atom(s) and/or the like, or may be a fused ring resulting from fusion of the hetero rings. As the hydrophobic ring, aromatic rings are preferred. Examples of the aromatic rings include benzene ring, naphthalene ring and anthracene ring. Among these rings, benzene ring and naphthalene ring are preferred, and benzene ring is most preferred.

Examples of preferred polymer used in the present invention include sodium polyanethole sulfonate, sodium polystyrene sulfonate (PS-1, PS-5, PS-50 and PS-100 (tradenames, produced by Tosoh Corporation), sodium salt of condensate between naphthalene sulfonic acid and formalin, sodium salt of condensates between an aromatic sulfonic acid and formalin (more concretely, DISROL (tradename, produced by Nippon Nyukazai Co., Ltd.), DEMOL (tradename, produced by Kao Corporation), POLITY PS-1900 (tradename, produced by Lion Corporation) and POLITY N-100K (tradename, produced by Lion Corporation).

Examples of the preferred polymers used in the present invention include those containing a recurring unit(s) represented by the following Formula [I]:

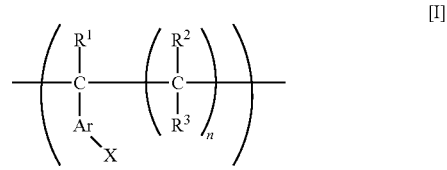

[I]

wherein Ar represents a hydrophobic ring; X represents the ionic functional group; R1 to R3 independently represent hydrogen or alkyl; n represents an integer of 0 to 10; hydrogen atom(s) bound to a carbon atom(s) constituting Ar optionally being substituted with a substituent(s) which does(do) not adversely affect the effect of the present invention.

In the above-described Formula [I], X and Ar represent the above-described ionic functional group and hydrophobic ring, respectively. In cases where R1 to R3 are alkyl groups, the alkyl groups are preferably lower ($C_1$-$C_4$, the same applies to the description below) alkyl groups. Further, n is preferably 0 to 3. The hydrogen atom(s) bound to a carbon atom(s) constituting Ar may optionally be substituted with a substituent(s) which does(do) not adversely affect the effect of the present invention. Examples of such a substituent include lower alkyl groups and lower alkoxy groups.

Among the recurring units represented by the Formula [I], those represented by the following Formula [II] are preferred:

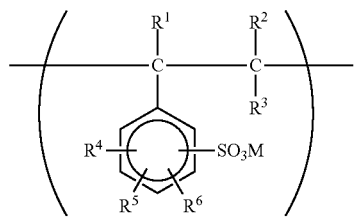

[II]

wherein M represents an atom or a group which becomes a monovalent cation in aqueous solution, preferably an alkaline metal such as sodium or potassium; $R^1$ to $R^3$ independently represent hydrogen or lower alkoxy; and $R^4$ to $R^6$ independently represent hydrogen or lower alkyl.

Among the recurring units represented by the above-described Formula [I], especially preferred are the anethole sulfonic acid salts represented by the following Formula [III], styrene sulfonic acid salts represented by the following Formula [IV], and salts of condensate between naphthalene sulfonic acid and formalin represented by the following Formula [V].

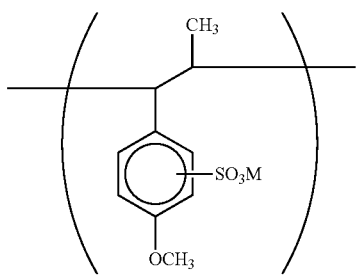

[III]

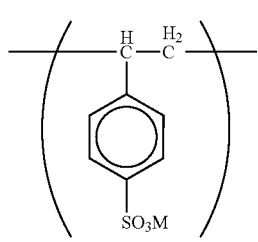

[IV]

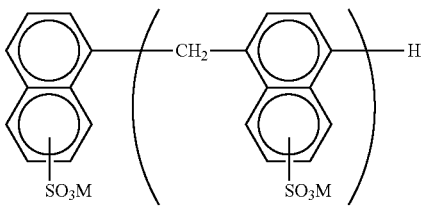

[V]

wherein in Formulae [III], [IV] and [V], M has the same meaning as in Formula [I], and is preferably an alkaline metal such as sodium or potassium.

The molecular weight of the polymer is preferably 1000 to 100,000, and more preferably 1000 to 60,000.

The above-described recurring units may be employed individually or two or more of them may be employed in combination. Although the polymer used in the present invention preferably consists of only the above-described recurring unit(s), the polymer may comprise other unit(s) to the extent that the effect of the present invention is not adversely affected. The content of such a unit(s) in the polymer is usually not more than 20 mol %, preferably not more than 10 mol %, still more preferably not more than 5 mol %.

The amount of the polymer(s) used in the present invention is not particularly limited, and is usually about 0.01 μg to 1 mg, preferably 0.1 μg to 0.1 mg per one immunochromatographic test strip. It is preferred, however, to select the amount optimum for attaining the effect, depending on the type of the macromolecular ionic surfactant, the type of the inorganic salt(s) used, composition and amount to be dropped of the test sample suspension, and so on.

To further eliminate the influences by the interfering substances, it is preferred to impregnate an inorganic salt(s) together with the polymer(s). Preferred examples of the inorganic salt include, but are not limited to, water-soluble inorganic compounds including sodium compounds, potassium compounds, cesium compounds, magnesium compounds, calcium compounds and strontium compounds, and combinations thereof. Preferred are sodium chloride, potassium chloride, lithium chloride, calcium chloride, magnesium chloride, sodium iodide, sodium bromide and the like. Sodium chloride and magnesium chloride are especially preferred.

The amount of the inorganic salt(s) used in the present invention is not particularly limited, and is usually about 0.01 μmol to 1 mmol, preferably 0.1 μmol to 0.1 mmol per one immunochromatographic test strip. It is preferred, however, to select the amount optimum for attaining the effect, depending on the type of the macromolecular ionic surfactant, the type of the inorganic salt(s) used, composition and amount to be dropped of the test sample suspension, and so on.

Based on the embodiment of FIG. 1, a method of using the test strip of the present invention will be described. Measurement is initiated by applying a specimen or a sample prepared using a specimen onto the sample pad. The test sample may be in the form of a preliminarily prepared suspension, or a specimen may be directly applied to the sample pad.

The test sample applied to the sample pad is developed in the horizontal direction sequentially to the labeled substance region, the support and the absorption band by capillary action. In the labeled substance region, the labeled antibody is released into the solution and developed to the support together with the development of the sample. In cases where an antigen is present in the sample, the antigen is specifically captured by a capture antibody in the detection regions of the support, and the antigen also forms a complex by a specific reaction with the labeled antibody. In this way, a sandwich of the antibodies via the antigen is established in the detection regions, and the labeled antibody-antigen complex can be measured in the detection regions.

In the method using the immunochromatographic test strip of the present invention, the test sample contacts the polymer(s) in which hydrophobic cyclic monomer(s) having an ionic functional group(s) is/are polymerized, and preferably contacts the polymer(s) and the inorganic salt(s), during the test sample develops from the sample pad to the labeled substance region, so that the influences by the interfering substances in the test sample are reduced.

Conventionally, to avoid the influences by the interfering substances in the test sample, a reagent for reducing the influences by the interfering substances is preliminarily added to a medium for forming a test suspension, and a specimen is suspended in the medium. However, since the specimen which is a biological sample is sampled with a swab or the like without quantification, the amount of the specimen varies. As a result, the medium for suspending the specimen may be diluted with an excess amount of the specimen and accordingly, the reagent for reducing the influences by the interfering substances may also be diluted so that a sufficient reducing effect may not be obtained, which is problematic. In the present invention, by using a member impregnating the polymer(s) in which hydrophobic cyclic monomer(s) having an ionic functional group(s) is/are polymerized, and preferably impregnating the polymer(s) together with the inorganic salt(s), which member is preliminarily arranged at a site upstream of the labeled substance region, and by always applying a fixed amount of the test sample to the sample pad, the reagent for reducing the influences by the interfering substances is not diluted to the extent that it loses its effect, so that an accurate and specific measurement can be attained.

The test sample to be subjected to the method of the present invention is not restricted, and biological samples with which the effect of the present invention, that is, to reduce the influence by the interfering substances is greatly exerted, are preferred. Preferred examples thereof include body fluids such as serum, blood plasma, blood, urine, feces, saliva, tissue fluids, spinal fluid and swabs, as well as dilutions thereof. Especially, test samples contaminated with substances originated from mucose membranes in the body, sputum, saliva, throat swab, nasal cavity swab, nasal aspirate, corner conjunctiva swab, feces specimen and the like are preferred.

In the method using the immunochromatographic test strip of the present invention, the test substance to be measured is an antigen or an antibody which can be measured by an immunoassay, that is, by an assay utilizing antigen-antibody reaction. The antigen may be any antigen as long as an antibody thereto can be prepared. Examples thereof include proteins, polysaccharides and lipids. Protozoa, *fungi, Bacteria, Mycoplasma*, rickettsiae, chlamydiae, viruses and the like containing these antigens can also be measured.

EXAMPLES

Hereinafter, the present invention will be described more specifically by way of examples thereof. However, the present invention is not limited to the following examples.

Examples 1 and 2, and Comparative Examples 1 to 4

Influences by Interfering Substances in Saliva and Effect of Reducing Influences by Interfering Substances by Conventional Method and by Method of Present Invention
1. Immobilization of Anti-*Mycoplasma pneumoniae* Antibody on Nitrocellulose Membrane A solution in which an anti-*Mycoplasma pneumoniae* antibody was diluted to a concentration of 1.0 mg/mL with purified water, and an anti-mouse IgG antibody were prepared. The anti-*Mycoplasma pneumoniae* antibody and the anti-mouse IgG antibody were applied linearly on the sample pad side and the absorption body side of a nitrocellulose membrane lined with a PET film, respectively. Thereafter, the nitrocellulose membrane was dried at 45° C. for 30 minutes to obtain an anti-*Mycoplasma pneumoniae* antibody-immobilized membrane. In this example, this membrane is referred to as an "antibody-immobilized membrane".
2. Immobilization of Anti-*Mycoplasma pneumoniae* Antibody on Colored Polystyrene Particles The anti-*Mycoplasma pneumoniae* antibody was diluted with purified water to a concentration of 1.0 mg/mL, and colored polystyrene particles were added thereto to a concentration of 0.1%. After stirring, carbodiimide was added to a concentration of 1%, and the resultant was further stirred. The supernatant was removed by centrifugation and resuspended in 50 mM Tris (pH 9.0), 3% BSA to obtain an anti-*Mycoplasma pneumoniae* antibody-bound colored polystyrene particles. In this example, these particles are referred to as "antibody-immobilized particles".
3. Application of Anti-*Mycoplasma pneumoniae* Antibody-Bound Colored Polystyrene Particles and Drying A prescribed amount of 1.0 µg of the antibody-immobilized particles prepared in section 2 were applied to a glass fiber non-woven fabric, and the resultant was dried at 45° C. for 30 minutes. In this Example, the thus obtained non-woven fabric is called "dried pad".
4. Preparation of Non-woven Fabric Impregnating Components for Reducing Effects by Interfering Substances Prescribed amounts of sodium polystyrenesulfonate (molecular weight: 14,000) and NaCl were applied to a non-woven fabric together with Tx100, and the resultant was dried to obtain a non-woven fabric impregnating components for reducing the effects by the interfering substances (per one test strip, 8 µg of sodium polystyrenesulfonate and 40 µmol of NaCl).
5. Preparation of *Mycoplasma pneumoniae* Test Strip The antibody-immobilized membrane prepared in section 1, the dried pad prepared in section 3, and the non-woven fabric impregnating components for reducing the effects by the interfering substances prepared in section 4 were attached to other members (the backing sheet and the absorption band) and the resultant was cut to a width of 5 mm to prepare *Mycoplasma pneumoniae* test strips. In this Example, the test strip using the non-woven fabric impregnating components for reducing the effects by the interfering substances as the sample pad is referred to as "test strip of the present invention". A similar test strip using a member to which nothing was applied in place of the non-woven fabric impregnating components for reducing the effects by the interfering substances prepared in section 4 was prepared and used in Comparative Examples. In this Example, the test strip using the non-woven fabric to which nothing was applied as the sample pad is referred to as "test strip of conventional method". The test strips included, from upstream of the flow of the test sample, a sample pad, a dried pad (labeled substance region), an antibody-immobilized membrane (detection region) and an absorption band.

6. Treatment With Saliva

A swab was placed in the mouth to make the swab well absorb saliva, and the resultant was suspended in a solution for treating test sample (Quicknavi-Sample Suspending Solution; produced by Denka Seiken Co., Ltd.) (saliva-treated test sample). A swab was placed in the mouth to make the swab well absorb saliva, and the resultant was suspended in a solution for treating test sample (Quicknavi-Sample Suspending Solution; produced by Denka Seiken Co., Ltd.) containing sodium polystyrenesulfonate (conventional method saliva-treated test sample).

7. Measurements

To the solution for treating test sample as it is, or to the saliva-treated test sample, *Mycoplasma pneumoniae* antigen was added and mixed, and each of the resultant mixtures, each in an amount of 50 was added dropwise to the test strip of the present invention and the test strip of conventional method, respectively. Fifteen minutes later, existence of deposited colored polystyrene particles on the prescribed site to which anti-*Mycoplasma pneumoniae* antibody was immobilized and the degree of the deposition were visually evaluated. The cases wherein the degree of the linear deposition was strong were evaluated as "+", the cases wherein the judgment was difficult were evaluated as "±", and the cases wherein no deposition was observed was evaluated as "−".

8. Results

The results are shown in Table 1.

TABLE 1

| Examples | Saliva Treatment | Test Strip | Evaluation Result |
|---|---|---|---|
| Comparative Example 1 | test sample suspension | No | conventional method | + |
| Comparative Example 2 | test sample suspension | Yes | conventional method | − |
| Example 1 | test sample suspension | No | the invention | + |
| Example 2 | test sample suspension | Yes | the invention | + |
| Comparative Example 3 | test sample suspension + sodium polystyrenesulfonate | No | conventional method | + |
| Comparative Example 4 | test sample suspension + sodium polystyrenesulfonate | Yes | conventional method | ± |

As shown in Table 1, with the conventional test strip (not containing sodium polystyrenesulfonate), the result of the judgment was "−" (false negative) for the test sample treated with saliva due to the interfering substances in the saliva in spite of the fact that the test sample contained the antigen in an amount which should be judged as "+" (positive) (Comparative Examples 1 and 2). Even when sodium polystyrenesulfonate was added to the test sample as described in Patent Document 1, the judgment was unclear for the saliva-treated test sample (Comparative Example 4). In contrast, when the test strip of the present invention was used, clear judgment was attained irrespective of whether the treatment with saliva was conducted or not (Examples 1 and 2). Further, in Comparative Example 2 in which a saliva-treated test sample was applied, deposition of the colored polystyrene particles was not observed not only at the site at which the anti-*Mycoplasma pneumoniae* antibody was immobilized, but also at the site at which the anti-mouse IgG antibody was immobilized. On the other hand, when sodium polystyrenesulfonate was added in liquid system (Comparative Example 4), which is a conventional method, although the deposition of the particles at the site at which the anti-mouse IgG antibody was immobilized was recovered, only a small degree of deposition was observed at the site at which the anti-*Mycoplasma pneumoniae* antibody was immobilized. In contrast to these conventional methods, in Example 2 in which the immunochromatographic test strip of the present invention (polystyrenesulfonate and the salt were impregnated) was used, the deposition of the particles was easily confirmed at both of the sites at which the anti-mouse IgG antibody was immobilized and at which the anti-*Mycoplasma pneumoniae* antibody was immobilized, respectively. Thus, it is apparent that by the method of the present invention, the effects by the interfering substances originated from the living body on the antigen-antibody reaction were effectively reduced when compared with the conventional methods.

Examples 11 to 17

Types of Polymers in Which Hydrophobic Cyclic Monomer Having Ionic Functional Group is Polymerized In the same manner as in Examples 1 and 2, test strips containing each of the commercially available surfactants (Table 2) containing a polymer in which a hydrophobic cyclic monomer having an ionic functional group is polymerized, in a prescribed amount (40 µg/test strip), were prepared. Using these test strips, by the same method as in Example 2, the effect of reducing the influences by the interfering substances in the saliva was examined. The results are shown in Table 2. As for the average molecular weights of the various surfactants, the average molecular weight of PS-1 is 10,000 to 30,000, that of PS-5 is 50,000 to 100,000, that of POLITY PS-1900 is 16,000, that of DEMOL NL is 3000 to 4000, and that of DEMOL EP is 7000 to 8000.

TABLE 2

| | Surfactant | Saliva Treatment | Test Strip | Judgment |
|---|---|---|---|---|
| Comparative Example 2 | no impregnation | Yes | conventional method | − |
| Comparative Example 5 | no surfactant | Yes | salt alone was impregnated | − |
| Example 3 | PS-1 (Tosho) | Yes | the invention | + |
| Example 4 | PS-5 (Tosho) | Yes | the invention | + |
| Example 5 | POLITY N100K (Lion) | Yes | the invention | + |
| Example 6 | POLITY PS-1900 (Lion) | Yes | the invention | + |
| Example 7 | DEMOL SSL (Kao) | Yes | the invention | + |
| Example 8 | DEMOL NL (Kao) | Yes | the invention | + |
| Example 9 | DEMOL EP (Kao) | Yes | the invention | + |
| Example 10 | sodium polyanethole sulfonate | Yes | the invention | + |

As shown in Table 2, the effect of impregnating any of the polymers was clearly observed even though the degree of the effect varies depending on the type of the polymer.

Example 3

Types of Inorganic Salts

In the same manner as in Examples 1 and 2, test strips containing a commercially available surfactant PS-1

(TOSOH) containing a polymer in which a hydrophobic cyclic monomer having an ionic functional group is polymerized, in a prescribed amount (2 μg/test strip), and containing each of various inorganic salts (Table 3) in a prescribed amount (4 μmol/test strip), were prepared. By the same method as in Example 2, the effect of reducing the influences by the interfering substances in the saliva was examined. The results are shown in Table 3.

TABLE 3

| | Inorganic Salts | Saliva Treatment | Test Strip | Judgment |
|---|---|---|---|---|
| Comparative Example 2 | no impregnation | Yes | conventional method | − |
| Example 11 | NaCl | Yes | the invention | + |
| Example 12 | KCl | Yes | the invention | + |
| Example 13 | KI | Yes | the invention | + |
| Example 14 | MgCl$_2$ | Yes | the invention | + |
| Example 15 | CaCl$_2$ | Yes | the invention | + |
| Example 16 | LiCl | Yes | the invention | + |
| Example 17 | NaBr | Yes | the invention | + |

It was confirmed that the influences by the interfering substances originated from a living body on the antigen-antibody reaction were reduced by using each of the various inorganic salts together with the commercially available surfactant containing a polymer in which a hydrophobic cyclic monomer having an ionic functional group is polymerized. Further, the effect to reduce the influences by the interfering substances was confirmed for all of the inorganic salts, even though the degree of the reducing effect varies depending on the type of the inorganic salt.

Example 18

Advantage of Using Polymer in which Hydrophobic Cyclic Monomer Having Ionic Functional Group is Polymerized Together with Inorganic Salt In the same manner as in Examples 1 and 2, test strips containing a commercially available surfactant PS-1 (tradename, TOSOH) containing a polymer in which a hydrophobic cyclic monomer having an ionic functional group is polymerized, in a prescribed amount (Table 4), and containing sodium chloride in a prescribed amount (Table 4), were prepared. By the same method as in Example 2, the effect of reducing the influences by the interfering substances in the saliva was examined. Further, the levels of background (resulted from the remaining particles on the membrane other than the test lines, and decrease the ease of visual observation) were also evaluated. The results are shown in Tables 4 and 5.

TABLE 4

| | | NaCl (μmol/test strip) | | | |
|---|---|---|---|---|---|
| | | 0 | 0.4 | 4 | 40 |
| PS-1 (μg/test strip) | 0 | − | − | − | − |
| | 0.8 | ± | + | + | + |
| | 8 | ± | + | + | + |
| | 80 | + | + | + | + |

\* The results shown within the thick frame are those of this Example.

TABLE 5

| | | NaCl (μmol/test strip) | | | |
|---|---|---|---|---|---|
| | | 0 | 0.4 | 4 | 40 |
| PS-1 (μg/test strip) | 0 | low | low | low | low |
| | 0.8 | low | low | low | low |
| | 8 | low | low | low | low |
| | 80 | high | low | low | low |

\* The results shown within the thick frame are those of this Example.

As shown in Table 4, when sodium polystyrenesulfonate (PS-1) alone was impregnated, the judgment was unclear at the low concentrations (clear at the high concentration), while by using both of sodium polystyrenesulfonate and sodium chloride, clear judgment was attained even for the cases where the concentration of sodium polystyrenesulfonate was low. Further, in the case where sodium polystyrenesulfonate alone was used, the background was high at the high concentration (Table 5) so that ease of visual observation was decreased, while in the case where sodium chloride was also used, the background was low even in the case where the concentration of sodium polystyrenesulfonate was high. From these, it can be seen that it is advantageous to use both of PS-1 and NaCl when compared with the cases where one of these alone is used.

DESCRIPTION OF THE SYMBOLS

1 support (containing detection regions)
2 labeled substance region
3 detection region
4 sample pad
5 absorption band
6 backing sheet

The invention claimed is:

1. An immunochromatographic test strip comprising, in the order from upstream, a sample pad, a labeled substance region, a detection region and an absorption band, wherein a polymer is impregnated at a region upstream of said labeled substance region,
   wherein at least one inorganic salt is impregnated together with said polymer, wherein the at least one inorganic salt is selected from the group consisting of NaCl, KCl, KI, MgCl$_2$, CaCl$_2$, LiCl and NaBr; and
   wherein said polymer is a polystyrene sulfonate or salt thereof.

2. An immunochromatography method comprising using said immunochromatographic test strip according to claim 1.

\* \* \* \* \*